United States Patent [19]

Meilland

[11] Patent Number: Plant 6,170

[45] Date of Patent: May 10, 1988

[54] ROSE PLANT—MEILARCO VARIETY

[75] Inventor: Marie-Louise Meilland, Antibes, France

[73] Assignee: The Conard-Pyle Company, West Grove, Pa.

[21] Appl. No.: 838,703

[22] Filed: Mar. 11, 1986

[51] Int. Cl.[4] ..... A01H 5/00

[52] U.S. Cl. ..... Plt./9

[58] Field of Search ..... Plt. 9

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided which forms in abundance highly attractive double blossoms having a romantic pale pink coloration and a long lasting quality on the plant. The new variety is well suited for pot forcing and exhibits a vigorous growth habit which forms compact and regular vegetation.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) of the new variety was an unnamed variety formed by crossing the Fashion variety (U.S. Plant Pat. No. 789) with the Meialfi variety. The male parent (i.e., the pollen parent) of the new variety was the variety Meidanego. The parentage of the new variety can be summarized as follows:

(Fashion × Meialfi) × Meidanego.

The seeds resulting from the above pollination were sown in a greenhouse and 12 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance attractive double blossoms which are pale pink in coloration and of long duration on the plant,
(b) is well suited for pot forcing, and
(c) exhibits a vigorous growth habit which results in the formation of compact and regular vegetation.

The new variety well meets the needs of the greenhouse floricultural industry and the horticultural industry for many usages. It is particularly well-suited for pot forcing and can be grown as attractive ornamentation in parks and gardens.

The new variety has been found to undergo asexual propagation by a number of routes, including budding, winter bench grafting, etc. The characteristics of the new variety have been found to be strictly transmissible by such asexual propagation from one generation to another.

The new variety has been named the Meilarco variety.

BRIEF DESCRIPTION OF THE PHOTOGRAPH

The accompanying photograph shows an nearly true as it is reasonably possible to make the same, in color illustration of this character, typical specimens of the plant parts of the new variety. The rose plants of the new variety described herein were one year old and observed during June while growing on their own roots outdoors at Cannet des Maures, France.

DETAILED DESCRIPTION

Figures 1, 2, 3, 4, 5, 6, 7, 8, 9, 10, 11, 12, 13, 14, 15:
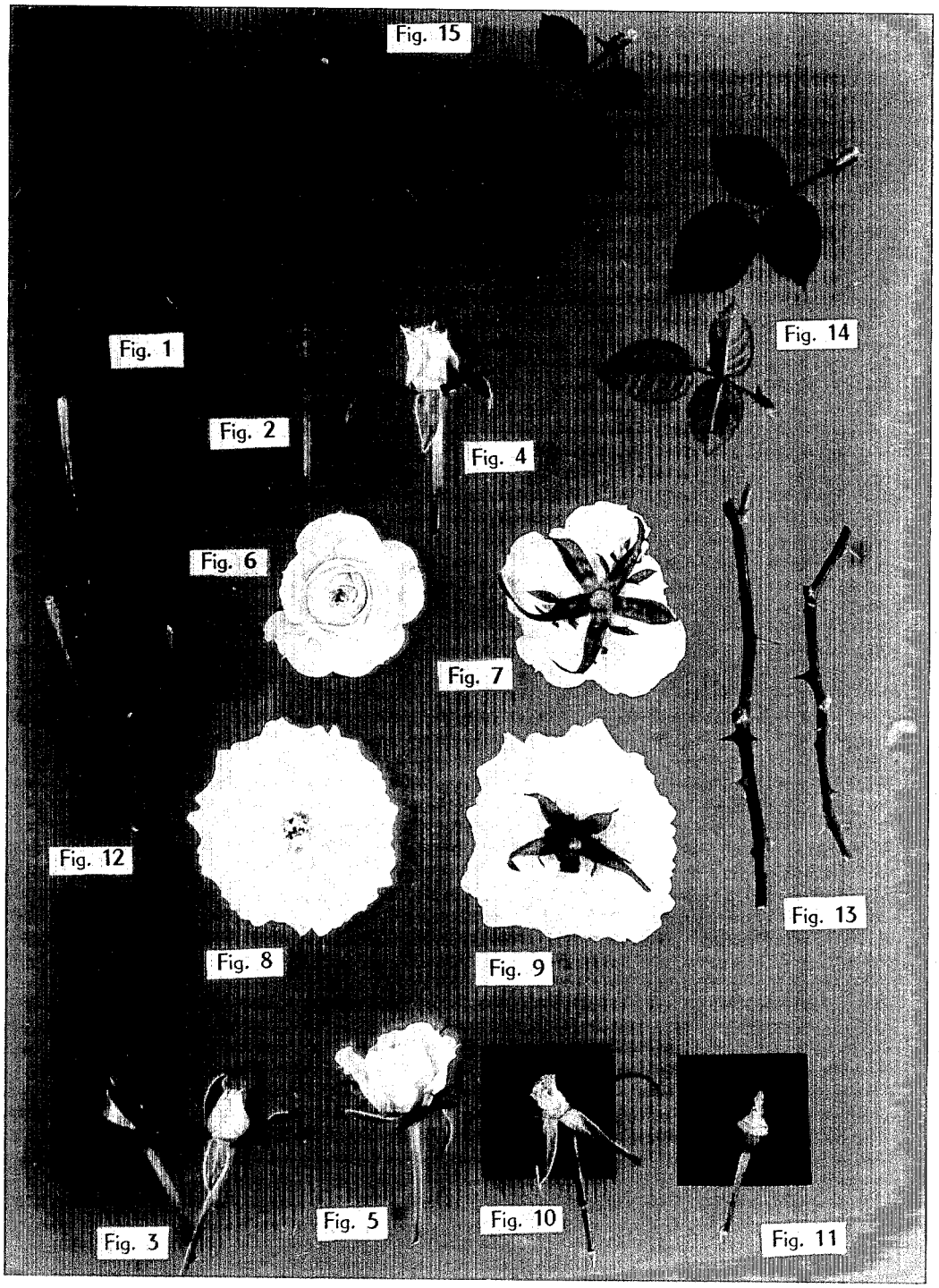
FIG. 1 illustrates a specimen of a young shoot.
FIG. 2 illustrates a specimen of a floral bud before the opening of the sepals.
FIG. 3 illustrates a specimen of a pair of floral buds at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates specimens of flowering stems.
FIG. 13 illustrates specimens of main branches.
FIG. 14 illustrates specimens of leaves with three leaflets with the upper surface being shown on the top and the under surface being shown on the bottom.
FIG. 15 illustrates specimens of leaves with five leaflets with the under surface being shown on the left and the upper surface being shown on the right.

The chart used in the identification of the colors is that of The Royal Horticultural Society (R.H.S. Colour Chart). The description is based on one year old specimens of the new variety during June while growing outdoors on their own roots in field soil at Cannet des Maures, France.

Class: Miniature.

Plant:

*Height.*—Approximately 30 cm. on average.

*Habit.*—Bushy.

Branches:

*Color.*—Young stems: Yellow-Green Group 144A, somewhat suffused with reddish brown. Adult wood: Yellow-Green, Group 146B.

Leaves:

*Petioles.*—Upper surface: noticeable veination, reddish brown on young foliage and light green on adult foilage with more or less glandular sides. Under surface: light green with several small hooked thorns.

*Leaflets.*—Number: 3, 5 (most often), and 7. Shape: elliptic. Serration: simple and regular. General appearance: dark green foilage which is brilliant and dense. Color (young foliage): upper surface: Yellow-Green Group 144A with reddish margins and somewhat suffused with reddish brown. under surface: Yellow-Green Group 144A with reddish edges. Color (adult foliage): upper surface: bright dark green, Yellow-Green Group 147A. under surface: medium green, Yellow-Green Group 147B.

Inflorescence:

*Number of flowers.*—Approximately 1 to 5 per stem.

*Peduncle.*—Medium green, straight, rigid and smooth, its length is approximately 6 cm. on average.

*Buds.*—Shape: egg-shaped. Length: approximately 2 cm. on average. Color upon opening: upper surface: pale pink, Red Group 36D, suffused with darker pink, Red Group 36C. under surface: similar to upper surface.

*Flower.*—Form: Well shaped, fully double. Diameter: approximately 6 to 7 cm. on average. Color (when opening begins): Upper surface: pale pink, Red Group 36D on external petals, and coral pink, Red Group 38D, on internal petals. under surface: pale pink, Red Group 36D, and more or less tinged with Red Group 36C. Color (when partially open): upper surface: pale pink, Red Group 36D on external petals, and coral pink, Red Group 38D on internal petals. under surface: pale pink, pink, Red Group 36D. Color (at end of opening): upper surface: pale pink, Red Group 36D, turning to white. under surface: pale pink, Red Group 36D, turning to white. Fragrance: slight. Lasting quality: long. Petal number: approximately 85 to 95 on average. Petal form: thick. Anthers: may have a few green centers on young plants.

I claim:

1. A new and distinct variety of Miniature rose plant characterized by the following combination of characteristics:

(a) forms in abundance attractive double blossoms which are pale pink in coloration and of long duration on the plant, (b) is well suited for pot forcing, and (c) exhibits a vigorous growth habit which results in the formation of compact and regular vegetation;

substantially as herein shown and described.

* * * * *